United States Patent
Logan, Jr. et al.

(10) Patent No.: US 7,936,453 B2
(45) Date of Patent: May 3, 2011

(54) TERAHERTZ FREQUENCY DOMAIN SPECTROMETER WITH INTEGRATED DUAL LASER MODULE

(75) Inventors: Ronald T. Logan, Jr., Pasadena, CA (US); Joseph R. Demers, Alhambra, CA (US); Bryon L. Kasper, San Marino, CA (US)

(73) Assignee: Emcore Corporation, Albuquerque, NM (US)

( * ) Notice: Subject to any disclaimer, the term of this patent is extended or adjusted under 35 U.S.C. 154(b) by 573 days.

(21) Appl. No.: 12/062,772

(22) Filed: Apr. 4, 2008

(65) Prior Publication Data
US 2010/0277726 A1 Nov. 4, 2010

(51) Int. Cl.
*G01N 21/21* (2006.01)
(52) U.S. Cl. .................... 356/300; 356/326; 250/339.07
(58) Field of Classification Search ........... 250/339.01–339.07; 356/300, 356/326
See application file for complete search history.

(56) References Cited

U.S. PATENT DOCUMENTS

| | | | |
|---|---|---|---|
| 5,379,309 A | 1/1995 | Logan, Jr. | |
| 5,623,145 A | 4/1997 | Nuss | |
| 6,304,219 B1 | 10/2001 | Rothe | |
| 6,348,683 B1 | 2/2002 | Verghese et al. | |
| 6,545,785 B1 | 4/2003 | Heflinger et al. | |
| 6,816,647 B1 | 11/2004 | Rudd et al. | |
| 6,844,552 B2 | 1/2005 | Zhang et al. | |
| 6,849,852 B2 | 2/2005 | Williamson | |
| 6,866,014 B2 | 3/2005 | Ciesta et al. | |
| 7,174,037 B2 | 2/2007 | Amone et al. | |
| 7,439,511 B2 * | 10/2008 | Demers ........................ 250/341.1 |
| 7,535,005 B2 * | 5/2009 | Demers ........................ 250/341.1 |
| 7,781,736 B2 * | 8/2010 | Logan et al. ............. 250/339.07 |
| 2006/0255277 A1 | 11/2006 | Cole et al. | |
| 2008/0212974 A1 | 9/2008 | Davies et al. | |
| 2009/0200472 A1 * | 8/2009 | Gregory .................... 250/339.07 |
| 2010/0080505 A1 | 4/2010 | Sartorius et al. | |

FOREIGN PATENT DOCUMENTS

| | | |
|---|---|---|
| EP | 1233527 A1 | 8/2002 |
| GB | 2381121 A | 4/2003 |

OTHER PUBLICATIONS

Blazar LUX5010 Multirate 4x10G Optical Active Cable; Luxtera (pp. 1-4).
English translation of abstract of EP1233527.1. 1 page. European Patent Office. http://ep.espacenet.com/?locale=en_EP.

* cited by examiner

*Primary Examiner* — L. G Lauchman (57) ABSTRACT

An apparatus for analyzing, identifying or imaging a target including an integrated dual laser module coupled to a pair of photoconductive switches to produce CW signals in the range of frequencies from 100 GHz to over 2 THz focused on and transmitted through or reflected from the target; and a detector for acquiring spectral information from signals received from the target and using a multi-spectral homodyne process to generate an electrical signal representative of some characteristics of the target with resolution less than 250 MHz. The photoconductive switches are activated by laser beams from the dual laser module. The lasers in the module are tuned to different frequencies and have two distinct low frequency identification tones respectively that are used in conjunction with a stable optical filter element to permit precise determination of the offset frequency of the lasers.

17 Claims, 8 Drawing Sheets

TERAHERTZ FREQUENCY DOMAIN SPECTROMETER WITH INTEGRATED DUAL LASER MODULE

GOVERNMENT RIGHTS STATEMENT

This invention was made with government support under Contract No. W911NF-05-C-068 awarded by the U.S. Army Research Office under a subcontract to Physical Domains LLC. The Government has certain rights in the invention.

REFERENCE TO RELATED APPLICATIONS

This application is related to U.S. patent application Ser. No. 11/796,069, filed Apr. 26, 2007 which is a continuation-in-part of U.S. patent application Ser. No. 11/669,685 filed Jan. 31, 2007, now U.S. Pat. No. 7,535,005.

BACKGROUND OF THE INVENTION

1. Field of the Invention

The invention relates to microwave, millimeter wave and submillimeter wave spectroscopy systems and components and in particular to an integrated dual laser module for use in a homodyne transceiver useful for terahertz spectroscopy.

2. Description of the Related Art

Terahertz devices and systems generally refer to creating and detecting electromagnetic energy between 300 GHz and 3 terahertz (3 THz), or wavelengths from 100 to 1000 microns (0.1 to 1.0 millimeters), and also referred to as the submillimeter or far-infrared region of the electromagnetic spectrum. Terahertz energy can be created, for example, using short-pulsed lasers, heterodyne lasers, electronic diode multipliers, free-electron lasers, and BWOs.

One important application of terahertz systems is in terahertz (THz) spectroscopy, and more particularly in time domain terahertz spectroscopy. In such systems, femtosecond pulses from a mode-locked laser are focused onto a suitable semiconductor material to produce THz radiation. The radiation is directed to the target or sample to be analyzed, and a detector or a detector array is used to collect the signal propagated through or reflected from the object. Since such measurements are made in the time domain by collecting the time sequence of pulses, the signals must then be processed by a Fourier transformation to recover the frequency domain spectral information.

Terahertz spectroscopy presents many new instrumentation and measurement applications since certain compounds and objects can be identified and characterized by a frequency-dependent absorption, dispersion, and/or reflection of terahertz signals which pass through or are reflected from the compound or object. Some current terahertz systems perform analyses in the time-domain by collecting that transmitted signal propagating through the object and then processing the information contained in those signals by a Fourier transformer to produce a spectral analysis. By scanning every point or "pixel" on that object, either on a focal plane or in successive focal planes at different ranges, it is also possible for such a system to perform imaging of the surface or interior cross-sections or layers of the object. This non-invasive imaging technique is capable of differentiating between different materials, chemical compositions, or molecules in the interior of an object. However, the Fourier transformation from the time domain into the frequency domain imposes limitations on the frequency resolution and upon the ability to look at specific frequency windows.

As noted in a review article by Peter H. Siegel in IEEE Transactions on Microwave Theory and Techniques, Vol. 50, No. 3, 915-917 (March 2002), terahertz time-domain spectroscopy was pioneered by Nuss and others at Bell Laboratories in the mid-1990s (B. B. Hu and M. C. Nuss, "Imaging with terahertz waves," Opt. Lett., vol. 20, no. 16, pp. 1716-1718, Aug. 15, 1995; D. M. Mittleman, R. H. Jacobsen, and M. C. Nuss, "T-ray imaging," IEEE J. Select. Topics Quantum Electron., vol. 2, pp. 679-692, September 1996), and recently commercialized by at least two companies, Picometrix, LLC of Ann Arbor, Mich. (D. D. Arnone et al., "Applications of terahertz (THz) technology to medical imaging," in Proc. SPIE Terahertz Spectroscopy Applicat. II, vol. 3823, Munich, Germany, 1999, pp. 209-219) and Teraview Ltd. (a spinoff of Toshiba Research Europe) located in Cambridge, England (D. Arnone, C. Ciesla, and M. Pepper, "Terahertz imaging comes into view," Phys. World, pp. 35-40, April 2000).

In situ measurements of the transmitted or reflected terahertz energy incident upon a small sample are processed to reveal spectral content (broad signatures only), time of flight data (refractive index determination, amplitude and phase, and sample thickness), and direct signal strength imaging. The principle involves generating and then detecting terahertz electromagnetic transients that are produced in a photoconductive switch (PCS) or a crystal by intense femtosecond optical laser pulses. The laser pulses are beam split and synchronized through a scanning optical delay line and made to strike the terahertz generator and detector in known phase coherence. By scanning the delay line and simultaneously gating or sampling the terahertz signals incident on the detector, a time-dependent waveform proportional to the terahertz field amplitude is produced. Fourier transformation of this waveform yields information about the frequency spectral content. Transverse scanning of either the terahertz generator or the sample itself allows a 2-D image to be built up over time.

Other developments include rapid scanning (S. Hunsche and M. C. Nuss, "Terahertz 'T-ray' tomography," in Proc. SPIE Int. Millimeter SubmillimeterWaves Applicat. IV Conf., San Diego, Calif., July 1998, pp. 426-433.) and true 2-D sampling using charge-coupled device (CCD) arrays (Z. Jiang and X.-C. Zhang, "Terahertz imaging via electrooptic effect," IEEE Trans. Microwave Theory Tech., vol. 47, pp. 2644-2650, December 1999.). In the Picometrix and Lucent Technologies systems, the generator and detector are based on the photoconductive effect in low-temperature-grown (LTG) gallium-arsenide (GaAs) compound semiconductor material, or radiation-damaged silicon on sapphire semiconductor. The Teraview system uses terahertz generation by difference-frequency mixing in a nonlinear crystal (ZnTe) and detection via the electrooptical Pockels effect (measuring the change in birefringence of ZnTe induced by terahertz fields in the presence of an optical pulse) as first demonstrated by Zhang at the Rensselaer Polytechnic Institute (RPI), Troy, N.Y. (see Q. Wu, T. D. Hewitt, and X.-C. Zhang, "Two-dimensional electro-optic imaging of THz beams," Appl. Phys. Lett., vol. 69, no. 8, pp. 1026-1028, Aug. 19, 1996.). The femtosecond optical pulses are currently derived from relatively expensive Ti:Sapphire lasers, but other proposals include longer wavelength, especially 1.5 micron, solid-state systems that can take better advantage of fiber technology (see D. M. Mittleman, R. H. Jacobsen, and M. C. Nuss, "T-ray imaging," IEEE J. Select. Topics Quantum Electron., vol. 2, pp. 679-692, September 1996). The RF signals produced by the optical pulses typically peak in the 0.5-2 THz range and have average power levels in the microwatt range and peak energies around a femtojoule. This makes T-ray imaging an attractive tool for medical applications (noninvasive sampling), as well as for nondestructive analysis of biological materials or electronic parts. The largest drawback of prior art designs is the need to scan the delay line slowly and over a distance of the desired wavelength resolution (e.g., a 1 GHz resolution would require a 7.5 cm scan of the movable optical delay line) and the inability to interrogate discrete frequencies of interest. The high degree of positional tolerance required to be maintained on the movable optical delay assembly limits the utility of this approach in applications where compact size and operation in uncontrolled environments are required with wide temperature excursions and/or shock and vibration. Also, in many cases, higher frequency resolution and accuracy are desired than is easily possible with scanning delay-line systems, such as in analysis of Doppler-limited molecular rotational transitions in low-pressure gases.

The need for a multi-octave tunable spectrometer in the THz region is justified by the new suite of applications relating to materials identification facing researchers and system developers today. Historically, the THz field has been dominated by radio astronomers and chemists usually aimed at detecting trace amounts of small gaseous molecules in the interstellar medium or in the Earth's upper atmosphere. The low pressure of the media involved would often lead to narrow, Doppler-limited absorption lines, sometimes less than 1 MHz in linewidth. In roughly the last decade, the THz landscape has changed dramatically with the discovery and demand for detection and imaging of larger molecules, particularly biomolecules and bioparticles. This includes, for example, proteins and vitamins using frequency sweeps above 1 THz, and bacterial spores and nucleic acids using frequency sweeps below 1 THz. Solid materials such as explosive agents and their precursors are also of particular interest for terahertz detection applications. Nano-structured materials are also of interest for high-resolution THz studies, due to the similarity in size of the nanostructures and the wavelength of THz radiation. In most cases the biomolecular and bioparticle absorption occurs not in the form of narrow lines, but rather as broad "signatures", typically 1 to 10 GHz or wider. Solid disordered materials typically have similarly broad absorption features due to phonons. Crystalline materials of interest may also exhibit sharper resonances. In many cases, there may only be a few limited frequency bands of interest that show strong THz absorption in a particular material of interest. A multi-octave spectrometer capable of measuring small discrete windows of frequencies allows faster measurement of signatures in the same session, increasing confidence and specificity.

In addition to the time-domain spectrometers noted above, frequency domain systems are also known (See the paper by Verghese et al., "Generation and detection of coherent terahertz waves using two photomixers," Appl. Phys. Lett., vol. 73, no. 26, pp. 3824-3826, Dec. 28, 1998.). One prior art terahertz spectrometer system is described in U.S. Pat. No. 7,291,835, assigned to the common assignee, and hereby incorporated by reference. The system includes a laser illumination arrangement that generates a pair of source laser beams incident on a source photomixer device or PCS to cause emission of subcentimeter radiation, at least a portion of which interacts with the remote sample to generate a "sample influenced radiation" which is then incident on a detector photomixer device. A second pair of laser beams is incident on the detector to produce an optical component of the detector photocurrent that is offset in frequency with respect to the detected source laser energy. As a result, the detector generates a frequency down-converted electrical output signal responsive to and characteristic of the sample-influenced radiation.

The concept of photomixing is known from U.S. Pat. No. 6,348,683 which describes a method of generating quasi-optical signals using an optical-heterodyne converter or photomixer source. Photomixer sources are compact solid-state sources that use two single frequency tunable lasers, such as diode lasers, to generate a terahertz difference frequency by photoconductive mixing in a photoconductive material. Photomixer sources using low-temperature-grown (LTG) GaAs have been used to generate coherent radiation at frequencies up to 5 THz. In particular the patent describes a transceiver for transmitting and receiving terahertz radiation. The transceiver includes a first light source that generates radiation at a first frequency and a second light source that generates radiation at a second frequency. The first and the second light source have a difference frequency that is approximately equal to the difference between the first and the second frequencies. A transmitter includes a first photomixer that is optically coupled to the first and the second light source. A first antenna is electrically coupled to the first photomixer. In operation, the first antenna radiates a signal generated by the first photomixer at the difference frequency. A receiver includes a second antenna positioned to receive the signal radiated by the first antenna. The second antenna generates a time varying voltage in response to the signal. A second photomixer is electrically coupled to the second antenna and is optically coupled to the first and the second light source. The second photomixer generates a current signal in response to the time varying voltage generated by the second antenna.

SUMMARY OF THE INVENTION

1. Objects of the Invention

It is an object of the present invention to provide an improved frequency domain terahertz spectrometer using two semiconductor lasers.

It is another object of the present invention to provide a terahertz spectrometer for the identification of a target spectrum with high resolution at low cost.

It is also another object of the present invention to provide a dual laser module for use in a frequency-domain terahertz spectrometer.

It is an object of the present invention to provide a method for discriminating the power from two source lasers in a composite optical beam.

It is another object of the present invention to provide a method for adjusting the frequency of each laser in a terahertz spectrometer to provide higher frequency specificity and resolution.

It is also another object of the present invention to provide adjustable resolution at specific frequency regions of interest.

It is still another object of the present invention to provide a field portable terahertz system in a highly compact configuration capable of identifying or imaging an object utilizing two lasers.

Some of the features of the inventions or embodiments of the invention may achieve fewer than all of the foregoing objects.

2. Features of the Invention

Briefly, and in general terms, the present invention provides a laser module including: a housing; a first laser assembly disposed in said housing for generating a first laser beam; a second laser assembly disposed in said housing for generating a second laser beam; a first beam splitter disposed in said housing in the path of said first and second beams for combining said beams into third and fourth optical beams; a second beam splitter disposed in said housing in the path of said third beam and producing fifth and sixth optical beams; a third beam splitter disposed in said housing in the path of the said fourth beam for producing seventh and eight optical beams; a first window in said housing in the path of said fifth beam for permitting said fifth beam to exit the housing; and a second window in said housing in the path of said seventh beam for permitting said seventh beam to exit the housing at right angles to said fifth beam.

In another aspect, the invention provides a method for determining the respective wavelengths (optical frequencies) of the optical frequency sources in a multi-optical frequency composite optical beam by applying a first low frequency tone to the first laser; applying a second low frequency tone, different from said first tone, to the second laser; combining the beams from the first and second lasers; splitting the combined beam into the said sixth and said eighth combined optical beams; detecting the power of the said eighth beam using a first photodiode having a first spectral response; detecting the power of the said sixth beam after it has passed through an optical filter with a defined transmission profile using a second photodiode having a second spectral response; and comparing the respective outputs of the first and second photodiodes and computing the wavelength of the first and second lasers.

In another aspect, the invention provides an apparatus for analyzing, identifying or imaging a target using an integrated laser module including first and second lasers; a source of constant wave (CW) radiation in the range of frequencies from 100 GHz to over 2 THz including a first PCS activated by an optical beam from said fifth beam resulting in a CW frequency that is the difference in frequencies of said first and second lasers; directing means such as an antenna or RF lens for causing said signals to be substantially simultaneously focused onto or through said target; and a detector for acquiring spectral information transmitted through the target or reflected from the target. The said seventh beam from the laser module is coupled to the detector PCS. Mixing of the difference in optical frequencies of the said seventh beam and the transmitted THz power in the detection PCS generates an electrical signal representative of some characteristic of the target.

Additional objects, advantages, and novel features of the present invention will become apparent to those skilled in the art from this disclosure, including the following detailed description as well as by practice of the invention. While the invention is described below with reference to preferred embodiments, it should be understood that the invention is not limited thereto. Those of ordinary skill in the art having access to the teachings herein will recognize additional applications, modifications and embodiments in other fields, which are within the scope of the invention as disclosed and claimed herein and with respect to which the invention could be of utility.

Some implementations or embodiments of the present invention may incorporate or implement fewer of the aspects and features noted in the foregoing summaries.

BRIEF DESCRIPTION OF THE DRAWINGS

These and other features and advantages of this invention will be better understood and more fully appreciated by reference to the following detailed description when considered in conjunction with the accompanying drawings wherein.

The novel features and characteristics of the invention are set forth in the appended claims. The invention itself, however, as well as other features and advantages thereof, will be best understood by reference to a detailed description of a specific embodiment, when read in conjunction with the accompanying drawings.

DETAILED DESCRIPTION OF THE PREFERRED EMBODIMENT

Details of the present invention will now be described, including exemplary aspects and embodiments thereof. Referring to the drawings and the following description, like reference numbers are used to identify like or functionally similar elements, and are intended to illustrate major features of exemplary embodiments in a highly simplified diagrammatic manner. Moreover, the drawings are not intended to depict every feature of actual embodiments or the relative dimensions of the depicted elements, and are not drawn to scale.

In the frequency-domain technique, CW THz radiation is produced through photomixing of the combined output of two single-frequency diode lasers in an ErGa:GaAs PCS. The wavelength of one (or both) of the lasers is tuned to vary the THz output frequency. In most spectroscopic applications of photomixing to date, the THz output beam from the PCS has been coupled to a sensitive broadband thermal detector (e.g., a liquid He bolometer or Golay cell), making the overall signal processing incoherent and phase insensitive. Coherent (homodyne) detection can be achieved at room temperature by mixing the same optical radiation from the diode lasers in a detector PCS onto which the THz signal is also incident. This provides greater sensitivity and faster data acquisition than the incoherent technique, and preserves phase information.

Some of the benefits of the coherent frequency-domain technique compared to the time-domain technique are: (1) no moving parts (i.e. no mechanical scanning delay line), (2) higher frequency resolution, and (3) the ability to selectively scan specific frequency regions of interest with adjustable resolution. Also, unlike pulsed systems, CW photomixing results in all of the THz power being concentrated at a single THz frequency, thus improving spectral density and signal-to-noise ratio at that frequency. However, previously it has been difficult to realize practical frequency-domain spectrometers due to the challenges associated with the construction and control of the dual lasers, namely mode-matching and co-collimation of the two laser beams and precise control of their difference frequency.

Figure 1A:
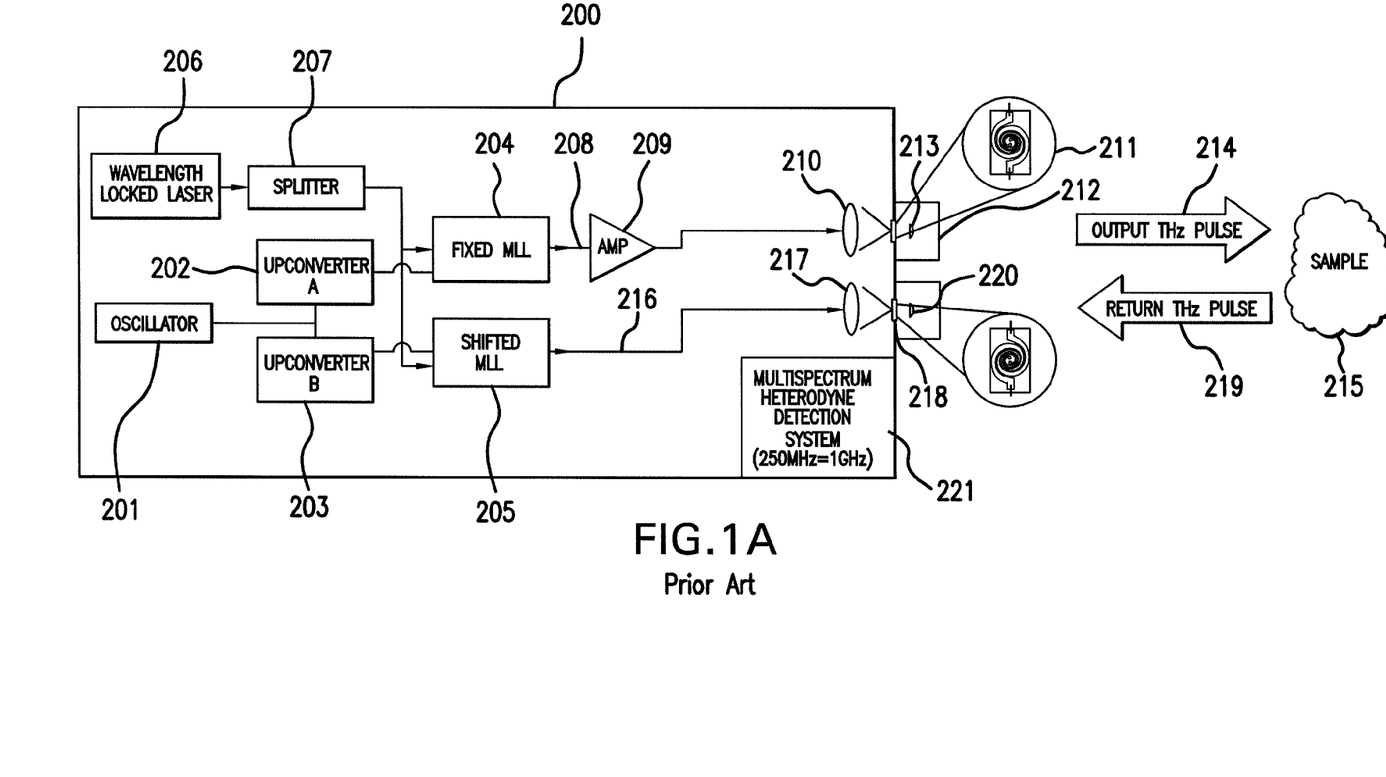
FIG. 1A is a block diagram of a frequency domain terahertz spectrometer known in the prior art which employs reflection from the sample.
Figure 1B:
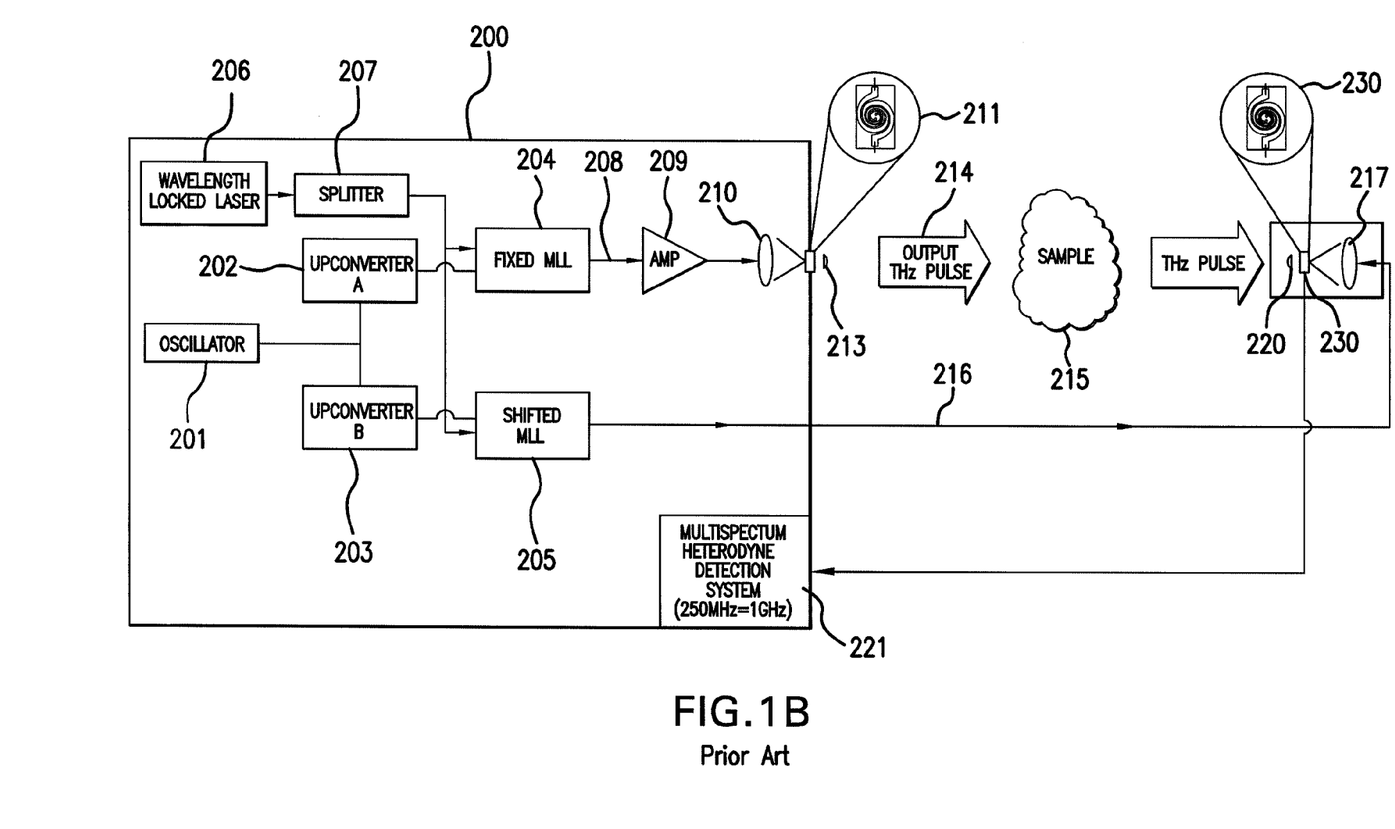
FIG. 1B is a block diagram of a frequency domain terahertz spectrometer known in the prior art which employs transmission through the sample.

FIGS. 1A and 1B depict frequency domain terahertz spectrometers known in the prior art. A prior art spectrometer as described in U.S. patent application Ser. No. 11/669,685, is depicted in the block diagram of FIG. 1A, which employs reflection from the sample, while FIG. 1B depicts a similar prior art spectrometer that employs transmission through the sample.

The FIGS. 1A and 1B show the spectrometer disposed in a housing 200, suited for portable use in the field. A crystal oscillator 201 produces a 1 KHz pulse which drives two upconverters 202 and 203 whose output is applied to a pair of mode locked lasers 204 and 205. The output of upconverter 202 is 100 MHz, and the output of upconverter 203 is 100.0025 MHz. The mode locked lasers are preferably 780 nm lasers of Calmar Optcom Inc. of Sunnyvale, Calif. The output of laser 204 is a comb of equally spaced pulses centered at 100 MHz, 200 MHz, 300 MHz, . . . 1000 GHz, 1000.100 GHz, etc. The output of laser 205 is a comb of equally spaced pulses at 100.0025 MHz, 200.005 MHz, 300.0075 MHz, . . . 1000.0025 GHz, 1000.1250025 GHz, etc. The lasers 204 and 205 may be driven by a wavelength locked laser 206, whose output is applied to a beam splitter 207; producing separate beams applied to lasers 204 and 205 respectively.

The output 208 of laser 204 is amplified by an optical amplifier 209, and the beam is in turn applied to a lens 210 which focuses the beam to a ten micron spot on the surface of a PCS 211. The frequency comb of optical pulses directed to the surface of the PCS semiconductor device produces terahertz radiation in the frequency range 100 GHz to over 2 THz. The terahertz frequency comb spectrum has a fundamental frequency $f_1$ and a series of harmonic components $2f_1$, $3f_1$, ... $nf_1$ ... which are integral multiples of the fundamental mode-locked frequency.

The terahertz radiation emitted from the PCS device 211 is collimated and collected by a silicon lens 213, preferably a hemispherically shaped structure approximately one centimeter in diameter. Additional lenses or other elements (represented generically as the attached unit 212), composed of Teflon may be placed downstream of the lens 213 to collimate the RF beams into the output THz pulse 214. Beam-shaping mirrors may also be used in lieu of or in addition to the silicon lens 213.

The target or object 215 to be identified will absorb and transmit some radiation, and also reflect a portion of the radiation back in the direction of the source or user, as shown by the return THz pulse 219. FIG. 1A depicts a prior art embodiment that utilizes the reflected radiation, while FIG. 1B utilizes transmitted radiation.

The output of the shifted mode-locked laser 205 is represented by beam 216 which is directed to a lens 217 which focuses the beam to a ten micron spot on the surface of a PCS 218 with a design similar to PCS 211, except the spiral arms are in the opposite direction, which acts as the detector. On the receiver side, the return signal 219 and the beam 216 are combined in the LTG GaAs PCS detector 218 to yield a heterodyne signal. This may be described as instantaneous multi-spectral heterodyne down conversion of the return signal. This frequency difference changes from a minimum of 2.5 KHz to a maximum of N times 2.5 KHz, where N is the number of locked modes, and typically the value of N may extend from N=1000 to N=20,000. Due to the extremely wide optical bandwidths of the laser gain media, it is not uncommon for mode-locked lasers to have hundreds of locked modes spanning more than 1000 GHz. Therefore it is possible to generate intensity modulation signals over this wide range of frequencies using the technique according to the present invention. The electrical output of the LTG GaAs detector 218 is in the form of electronic RF signals, which in the case of a spectrometer is processed in generically labeled block 221 in the unit 200 to analyze the data and thereby identify the object or a compositional characteristic thereof, such as the identity of the chemical compounds or material structures contained in the target or object.

In the FIG. 1B embodiment, the components are the same as in the FIG. 1A embodiment, so the above description of each of the components in FIG. 1A need not be repeated. In the FIG. 1B embodiment, the placement of the detector PCS 230 is configured so that it is located on the other side of the sample 215 so that the terahertz radiation 214 is transmitted through the sample 215 before being received by the detector PCS 230. Another difference in the PCS detector is that the direction of the spiral arms of the PCS 230 is oriented in the same direction as that of PCS 211.

Figure 2:
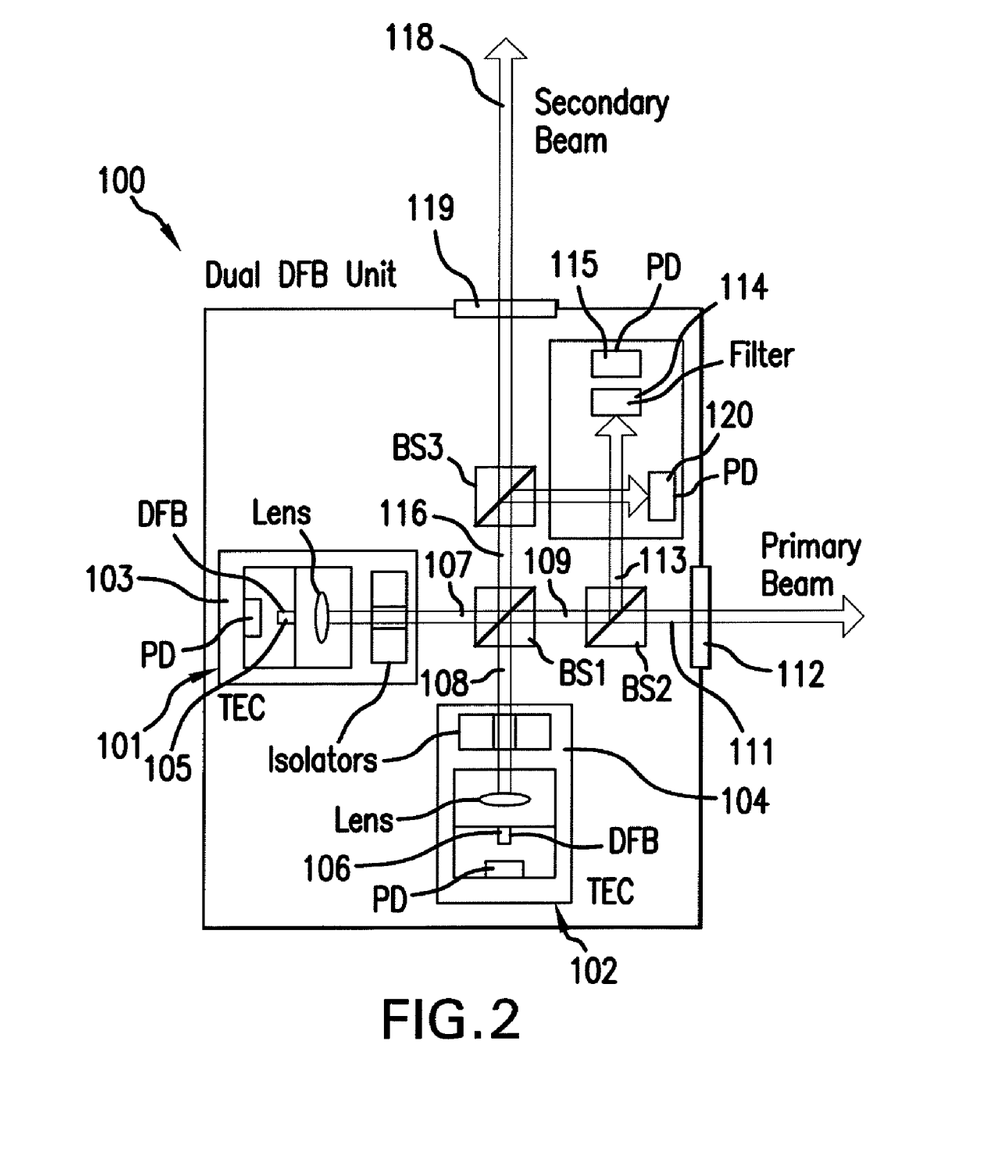
FIG. 2 is a block diagram of the dual laser module according to the present invention.
Figure 3:
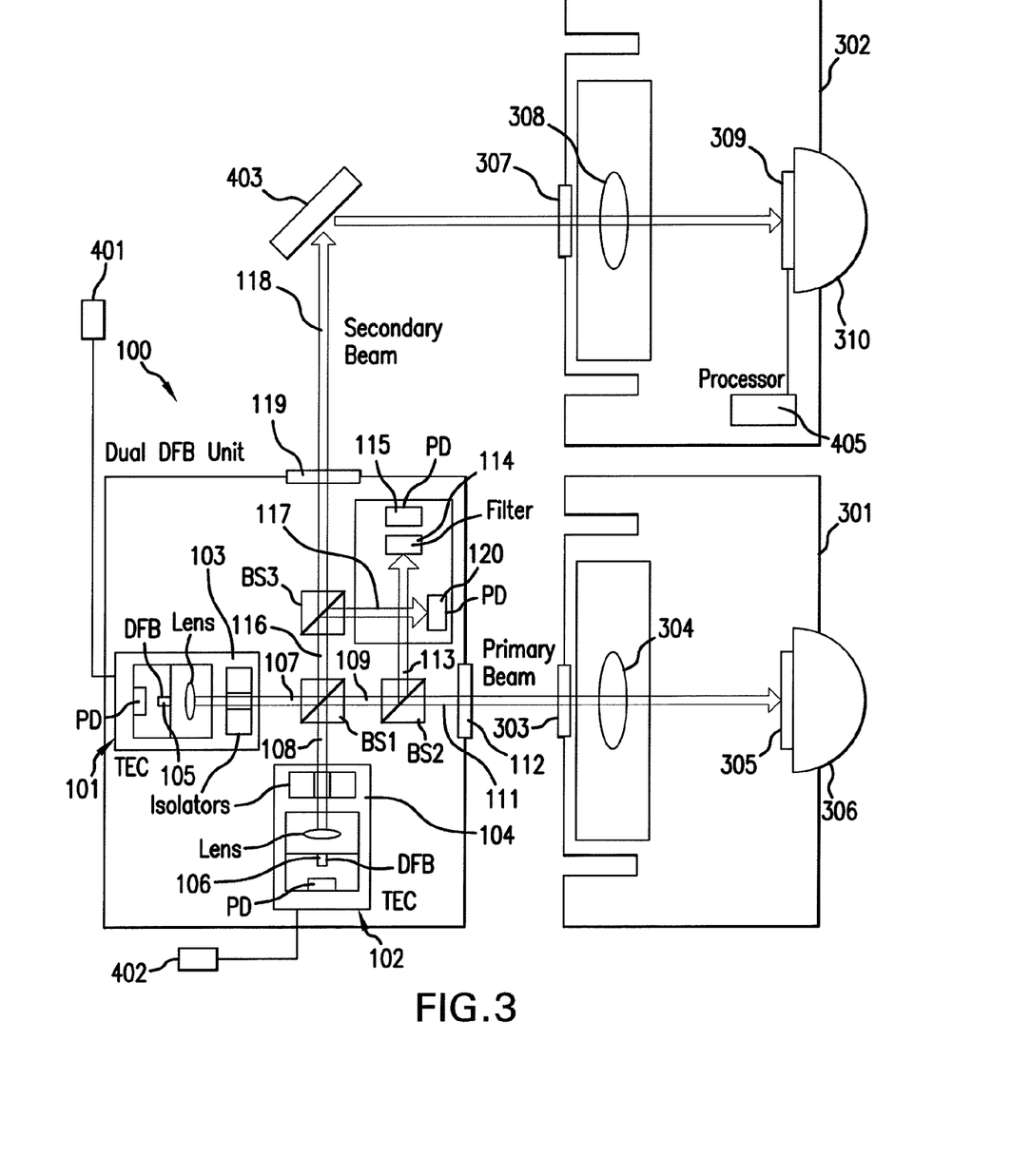
FIG. 3 is a block diagram of a terahertz spectrometer according to the present invention.

The dual laser module and the spectrometer of the present invention are depicted in the block diagrams of FIGS. 2 and 3 respectively. The key component of the coherent frequency domain THz spectrometer provided by the present invention is a highly-integrated dual semiconductor laser module 100.

The spectrometer depicted in FIG. 3 may employ reflection or transmission through the target or sample by appropriate placement of the source head 301 and the detector head 302, and may further incorporate a processor and other electronics for determining the identity or composition of the target, and/or printing or displaying the results so that the information is readily available to the user.

Figure 4:
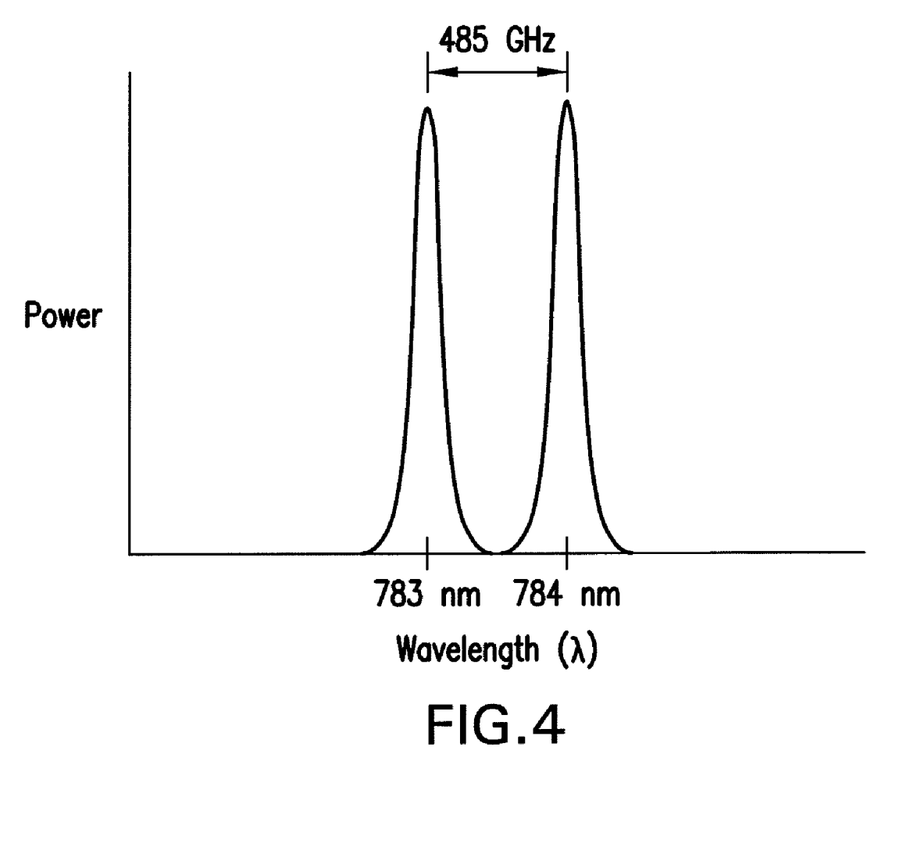
FIG. 4 is a graph illustrating the optical frequency spectrum showing the output of the two lasers in the laser module of FIG. 2.

FIG. 2 depicts a housing 100 incorporating the optical components, suited for incorporation as a subassembly in the spectrometer of FIG. 3. The lasers 105 and 106 are preferably two 783 nm distributed feedback (DFB) or distributed Bragg reflector (DBR) lasers with single-longitudinal-mode and single spatial-mode operation over the desired range of wavelengths, available from various vendors (see for example Eagleyard Photonics GmbH of Berlin, Germany.) In the present invention it would also be possible to utilize one or more external-cavity tunable semiconductor lasers such as are available from Emcore Corporation Also, it is noted that two or more DFB or DBR lasers could be fabricated on a common semiconductor substrate with a semiconductor waveguide combiner element to produce a single optical output containing both laser frequencies. The optical spectrum of the output of the lasers 105, 106 is depicted in FIG. 4 which depicts the dual frequency output of these narrow line width lasers. In this particular embodiment, the output of one laser is adjusted to 783 nm, and the output of the other laser is at 784 nm. Key aspects of the present invention are to provide suitable diode laser packaging including co-collimation of the laser beams to a very high degree of precision, very precise frequency control of the lasers, and monitoring the laser output through digital signal processing to achieve more accurate control over the laser output beam frequencies and achieve a resolution of less than 250 MHz in a terahertz spectrometer.

In one embodiment, the laser diode chips 105 and 106 are mounted on independent Peltier thermoelectric coolers (TECs) 103 and 104. The center wavelengths of the lasers are nominally 783 nm at 25° C., but the wavelengths may be temperature-tuned with a tuning coefficient of approximately 0.1 nm per ° C. Therefore, a temperature range of operation from −10 C to 40 C will yield a frequency range of approximately 5 nm. For the purposes of illustration only, if the DFB lasers are selected such that their center wavelengths at 25 C are at 782 nm and 784 nm, respectively, then a thermal tuning range of −10 C to +40 C on each laser chip will permit generation of offset wavelengths from 0 nm to approximately 7 nm, corresponding to a range of offset frequencies from 0 Hz to 3.4 THz. The thermal mass on the controlled surface of the TECs is kept to a minimum which allows for rapid frequency tuning. In the case of DBR laser diode chips, the Bragg-reflection section of each laser is adjusted electronically to vary the laser frequency. Wider offset frequency ranges may also be possible by employing wider temperature excursion, or by using DBR lasers. The output from each laser is collimated with an aspheric lens mounted on a precision lens-mount with sub-micron adjustment capability (see, e.g. U.S. Pat. No. 7,126,078). The laser outputs are directed through optical isolators to prevent feedback into the lasers. A 50/50 beamsplitter BS1 is disposed in the path of the output beams 107 and 108 and is used to co-collimate the two beams into composite primary and secondary beams 109 and 116, which are at right angles to each other. The lenses and the beamsplitter BS1 are carefully adjusted so that the beam overlap is optimized for generation of photomixing products.

In the present invention, the output beam 109 is directed along a first path to be coupled to a second beamsplitter BS2, and the second beam 116 is directed along a path and coupled to a third beamsplitter BS3. The optical propagation path downstream of the lasers and throughout the unit 100 may be either free space or an appropriate single-mode polarization-maintaining optical fiber (PMF). In the case of optical fiber construction, the beamsplitters would be replaced with suitable optical waveguide couplers. The basic topology is depicted in FIG. 2 and FIG. 3 using free-space optical implementation to more easily illustrate the various optical paths.

The second beam splitter BS2 also produces primary 111 and secondary 113 beams which are at right angles to one another. The secondary beam 113 is applied to a filter 114, and then to a first photodiode 115. The output of the photodiode 115 is used to sample and measure the power of the composite beam 109, as will be subsequently described. The primary beam 111 is directed to a window 112 in the module 100.

The third beam splitter BS3 also produces a primary and a secondary beam at right angles to one another. The primary beam 117 is applied to a second photodiode 120. The output of the photodiode 120 is used to sample and measure the power of the composite beam 116, as will be subsequently described. The secondary beam 118 is directed to a window 119 in the module 110.

FIG. 3 is a highly simplified block diagram that illustrates the integration of the dual laser module 100 into a spectrometer. In particular, the Figure depicts a first current source 401 which is coupled to laser 105 to drive it and modulate it with a low frequency 416 kHz tone, and a second current source 402 which is coupled to laser 106 and modulates it with a second low frequency 430 kHz tone. The use of such tones in connection with the composite optical signal will be subsequently discussed. Other tone frequencies may be selected as convenient.

A reflector element 403 in the path of secondary beam 118 is also depicted, as well as the source head 301 and the detector head 302.

The output beam 111 of the second beamsplitter BS2 exits the housing 100 through the window 112. This "primary beam" 111 is applied to a window 303 in the appropriately positioned source head 301, and then to a lens 304 in the source head 301 which focuses the beam to a spot of approximately ten microns in diameter on the surface of a PCS 305. The optical frequency signal directed to the surface of the PCS semiconductor device produces terahertz radiation from the PCS 305 in the frequency range 100 GHz to over 2 THz, corresponding to the offset frequency between the lasers 105 and 106.

The terahertz radiation emitted from the PCS device 305 is collimated and collected by a silicon lens 306 mounted to the source head 301. The lens 306 is preferably a hemispherically shaped structure approximately one centimeter in diameter. Additional lenses (not shown), composed of Teflon may be placed downstream of the lens 306 to collimate the RF beams into the output THz beam. Beam-shaping mirrors may also be used in lieu of or in addition to the silicon lens.

The target or object to be identified will absorb and transmit some radiation, and also reflect a portion of the radiation back in the direction of the source or user, in the manner shown by the return THz beam to the detector in FIG. 1A or 1B.

As noted above, the second beam 116 is coupled to a third beamsplitter BS3. The secondary beam 118 from beamsplitter BS3 exits the module 100 through a window 119, and is subsequently directed to the detector head 302. The secondary beam 118 is applied to a window 307 in the detector head 302, and then to a lens 308 which focuses the beam to a spot of approximately ten microns in diameter on the surface of a PCS 309. The silicon lens 310 collects the transmitted or reflected radiation from the target, which is then detected by PCS 309 in the same manner as the systems depicted in FIGS. 1A and 1B, and processed by processor 405 coupled to the PCS 309.

A terahertz frequency domain spectrometer is implemented using two ErAs:GaAs PCSs in a highly compact configuration, utilizing all solid-state components and no moving parts. The system utilizes a single package integration of two 783 nm DFB laser diodes with a high-resolution wavelength discriminator. Digital signal processing electronics provide precise frequency control and yield approximately 200 MHz accuracy of the THz signal frequency. Continuous frequency sweeping has been demonstrated with better than 500 MHz resolution from 100 GHz to 1.85 THz. The coherent detection sensitivity is shown to be in good agreement with previous theoretical predictions and yields a signal-to-noise ratio of 90 dB/Hz at 100 GHz and 60 dB/Hz at 1 THz through a path length in air of one foot. The spectrometer frequency resolution and dynamic range are suitable for applications involving analysis of chemical, biological, and explosive materials in solid-phase and gas-phase at atmospheric pressure.

Another feature of the present invention is to provide a method and apparatus for determining the respective wavelength of the lasers in a composite laser beam which has two optical beam sources at different frequencies. A determination of the wavelength of each source 105 and 106 in the primary beam emitted from the laser module 100 is an example of an application of such a method, since the spectroscopy applications contemplated by the present invention require such accuracy.

The electrical output of the photodiodes 115 and 120 would be a composite of a DC signal (representing the CW laser output) together with a small AC signal (representing the low frequency identification tone) superimposed on the DC signal. Since the composite signal is composed of two modulated DC signals, i.e. one from each of the modulated lasers 105 and 106, the goal of the signal processing applied to the composite signal is to recover the original two modulation signals and to precisely measure their relative amplitudes.

Digital filtering techniques can be used to separate the two signals since the modulation tones are different and of distinguishable frequencies.

More particularly as noted above, the method is preferably implemented in the present invention by applying a first low frequency tone to the first laser 105, and a second low frequency tone, different from the first tone, to the second laser 106.

Figure 5:
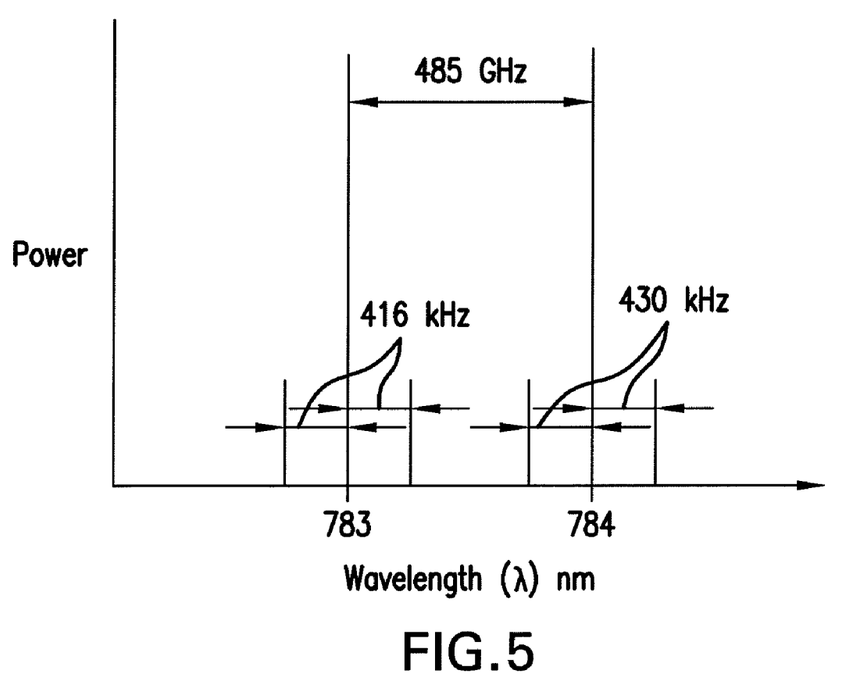
FIG. 5 is a simplified graph illustrating the composite optical frequency spectrum of the output beam from the two lasers in the laser module after distinct identification tones have been applied to each laser.

As described above in connection with FIGS. 2 and 3, a beam splitter is then disposed in the path of the composite beams 109 and 116 to produce first and second composite optical beams 113 and 117. The modulated composite beams would have a spectrum illustrated in FIG. 5.

A first photodiode 115 is disposed in the path of the first composite beam 113, and a second photodiode 120 is disposed in the path of the second composite beam 117. The photodiodes are arranged or adapted to have different known responses to various optical frequencies. One simple way to implement this arrangement is to use two identical photodiodes with a multi-layer thin-film optical filter 114 disposed in front of one (e.g. photodiode 115).

Figure 6:
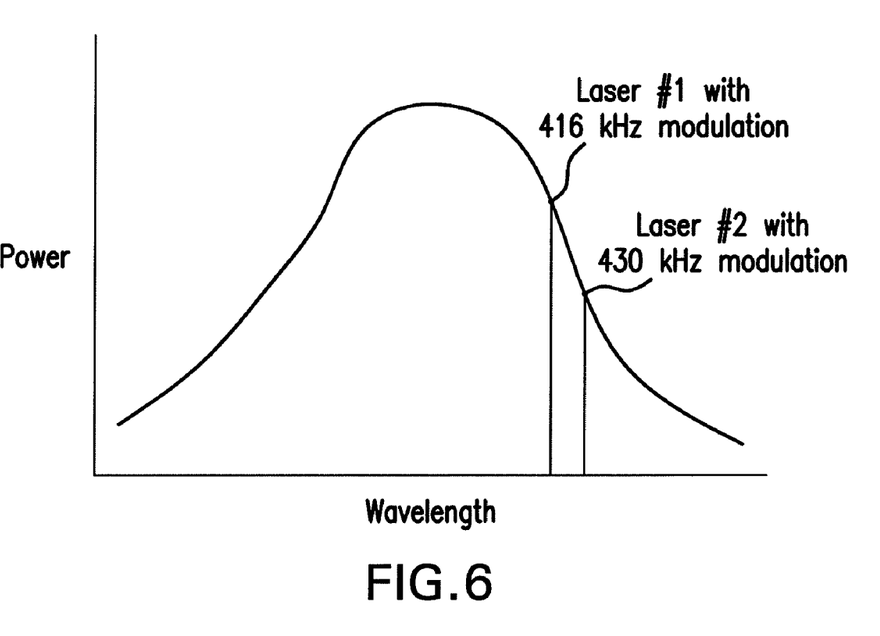
FIG. 6 is a graph of the filter profile of the optical filter used in the laser module according to the present invention.

FIG. 6 is an illustration of the filter spectral profile which may be used in determining the respective wavelength of two different lasers from a composite beam as implemented in the integral module according to the present invention. In this Figure, the power on the photodiodes 115 and 120 is graphed as a function of wavelength. The two laser frequencies that are modulated by unique low frequency tones, of 416 kHz and 430 KHz, are positioned on the graph.

An important aspect of photomixing spectroscopy is frequency metrology. To measure the laser frequencies, 20% of the primary beam is coupled through an optical filter 114 that has a predetermined wavelength profile and is then incident on a photodiode 115. The same amount of power is coupled out of the secondary beam 116 and is incident on an unfiltered photodiode 120. Since the two DFB lasers 105, 106 are current-modulated at slightly different frequencies, it is possible to distinguish their individual power levels on the filtered (115) and nonfiltered (120) photodiodes with a simple frequency-sensitive detection technique. By thermal stabilization of the optical filter with a separate TEC, absolute frequency stability of better than 100 MHz can be achieved. After initial calibration, comparison of the relative amplitudes of the lasers on these two photodiodes indicates accurately their respective wavelengths to within about 100 MHz. After photomixing, this measurement translates into a THz frequency accuracy of about 200 MHz. To measure the spectral purity of the system the lasers were offset in optical frequency by 10 GHz, as measured on a Burleigh WA-1500 wavemeter, and then focused onto a high-speed photodiode. The output was recorded on a RF spectrum analyzer. The FWHM linewidth of the photomixing signal is under 20 MHz, limited by the instantaneous linewidths of the DFB lasers.

In addition, in the present invention, the source PCS is electronically chopped at a baseband frequency in the range of DC to several MHz using a differential signal with amplitude from +Vchop to −Vchop. Chopping is typically used in conjunction with coherent homodyne detection as described above so that a lock-in amplifier tuned to the chopping frequency can be employed to limit the detection noise bandwidth. In previous optical chopping techniques, the optical beam illuminating the PCS is chopped with a segmented vane chopper as known in the art. Since the generated THz voltage is proportional to the incident laser power times the bias voltage applied across the PCS terminals, electronic chopping with a differential signal produces twice the peak THz voltage amplitude from the PCS, which leads to a factor of 4 improvement in generated THz signal power for a given level of optical illumination compared to optical chopping. This leads to a typical 6 dB improvement in signal-to-noise ratio of the present invention, compared to coherent detection with optical chopping.

Figure 7:
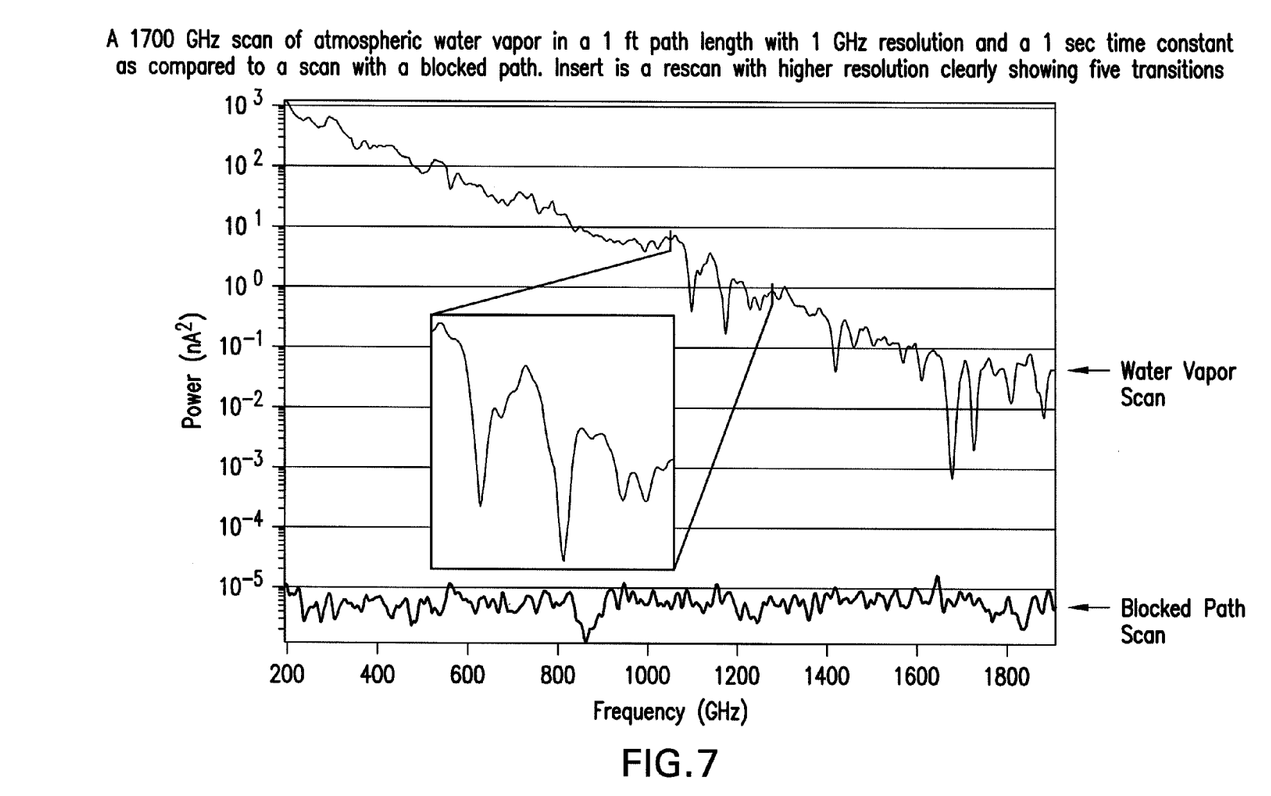
FIG. 7 is a graph illustrating the results of a scan of a target by the spectrometer of the present invention showing the resolution achievable.

FIG. 7 illustrates the efficacy of the spectrometer of the present invention by illustrating a 1700 GHz scan of atmospheric water vapor (graph I) and a similar scan of a solid obstruction (graph II). The test conditions were a one foot path length, a one GHz resolution, and a one second time constant. The enlarged insert depicts a high resolution scan according to the present invention showing higher resolution measurements of the transitions that appeared in the low resolution scan.

In summary, the present invention provides a compact frequency-domain terahertz coherent spectrometer with continuous tuning from 100 GHz to over 2 THz. The construction employs highly compact photonic integration techniques, electronic differential chopping, and room-temperature coherent THz detection. It is anticipated that the spectrometer will be useful for rapid identification of chemical, biological and explosive materials in solid-phase and gas-phase forms at standard atmospheric pressure. The highly integrated photonic assembly employing semiconductor diode lasers employs no moving parts and is inherently rugged and well-suited to field-deployable applications. Also, the coherent (homodyne) detection technique provides excellent SNR in agreement with theory, with much faster data acquisition times and no cryogenic cooling as required by the liquid He bolometers in more common (incoherent) THz photomixing spectrometers.

Various modifications and improvements of the present invention may also be apparent to those of ordinary skill in the art. Thus, the particular combination of parts described and illustrated herein is intended to represent only certain embodiments of the present invention, and is not intended to serve as limitations of alternate devices within the spirit and scope of the invention.

Various aspects of the techniques and signal processing apparatus of the present invention may be implemented in digital circuitry, or in computer hardware, firmware, software, or in combinations of them. Circuits of the invention may be implemented in computer products tangibly embodied in a machine-readable storage device for execution by a programmable processor, or on software located at a network node or web site which may be downloaded to the apparatus automatically or on demand. The foregoing techniques may be performed by, for example, a single central processor, a multiprocessor, one or more digital signal processors, gate arrays of logic gates, or hardwired logic circuits for executing a sequence of signals or program of instructions to perform functions of the invention by operating on input data and generating output. The methods may advantageously be implemented in one or more computer programs that are executable on a programmable system including at least one programmable processor coupled to receive data and instructions from, and to transmit data and instructions to, a data storage system, at least one in/out device, and at least one output device. Each computer program may be implemented in a high-level procedural or object-oriented programming language, or in assembly or machine language if desired; and in any case, the language may be compiled or interpreted language. Suitable processors include, by way of example, both general and special purpose microprocessors. Generally, a processor will receive instructions and data from read-only memory and/or random access memory. Storage devices suitable for tangibly embodying computer program instructions and data include all forms of non-volatile memory, including by way of example, semiconductor devices, such as EPROM, EEPROM, and flash memory devices; magnetic disks such as internal hard disks and removable disks; magneto-optical disks; and CD-ROM disks. Any of the foregoing may be supplemented by or incorporated in, specially designed application-specific integrated circuits (ASICS).

It will be understood that each of the elements described above, or two or more together, also may find a useful application in other types of constructions differing from the types described above.

While the invention has been illustrated and described as embodied in terahertz transceiver or spectrometer system, it is not intended to be limited to the details shown, since various modifications and structural changes may be made without departing in any way from the spirit of the present invention.

Without further analysis, from the foregoing others can, by applying current knowledge, readily adapt the present invention for various applications. Such adaptations should and are intended to be comprehended within the meaning and range of equivalence of the following claims.

The invention claimed is:

1. A laser module comprising:
a housing;
a first laser assembly disposed in said housing including a first laser for generating a first laser beam;
a second laser assembly disposed in said housing including a second laser for generating a second laser beam;
a beam splitter disposed in said housing in the path of said first and second beams for combining said beams into third and fourth optical beams;
a second beam splitter disposed in said housing in the path of said third beam and producing fifth and sixth beams; and
a first window in said housing in the path of said fifth beam for permitting said fifth beam to exit the housing.

2. A laser module as defined in claim 1, wherein said second laser assembly further comprises a focusing lens in the path of the second laser beam, and an isolator in the path of the output beam emitted from said focusing lens.

3. A laser module as defined in claim 2, wherein said first laser assembly comprises a thermoelectric cooler.

4. A laser module as defined in claim 1, further comprising:
a third beam splitter disposed in said housing and in the path of said fourth beam, and functioning to split said fourth beam into seventh and eight beams; and
a second window in said housing in the path of said seventh beam for permitting said seventh beam to exit the housing.

5. A laser module as defined in claim 1, further comprising a photodetector module disposed in said housing, including a first photodetector in the path of said sixth beam and a second photodetector in the path of said eighth beam, for measurement of the respective power of said first and second laser beams.

6. A laser module as defined in claim 1, further comprising a wavelength filter in the path of said sixth beam in front of said first photodetector.

7. A laser module as defined in claim 1, wherein said first and second lasers are distributed feedback lasers current modulated at slightly different frequencies.

8. A laser module as defined in claim 1, wherein said first and second beams are orthogonal to each other.

9. An apparatus for analyzing, identifying or imaging a target, comprising:
an integrated laser module including first and second laser, said integrated laser module comprising:
a housing;
a first laser assembly disposed in said housing including the first laser for generating a first laser beam;
a second laser assembly disposed in said housing including the second laser for generating a second laser beam;
a beam splitter disposed in said housing in the path of said first and second laser beams for combining said first and second laser beams into first and second composite optical beams;
a second beam splitter disposed in said housing in the path of the first composite optical beam and producing third and fourth optical beams; and
a first window in said housing in the path of said third optical beam for permitting said third optical beam to exit the housing;
a source of CW signals in the range of frequencies from 100 GHz to over 2 THz including a first photoconductive switch activated by said third optical beam;
directing means for causing said signals to be substantially simultaneously focused on or through said target; and
a detector for acquiring spectral information reflected from said target and coupled to said second composite optical beam for generating an electrical signal representative of some characteristic of the target.

10. An apparatus as in claim 9, wherein said detector includes a second photoconductive switch activated by said second composite optical beam.

11. An apparatus as defined in claim 9 further comprising a processor coupled to said detector for analyzing said electrical signal and determining a characteristic of said target based upon the absorption characteristics of said target in the 100 GHz to over 2 THz frequency band.

12. An apparatus as defined in claim 9, wherein said lasers are DFB or DBR lasers with different frequencies.

13. An apparatus as defined in claim 9, wherein each of the lasers are modulated with different low frequency identification tones.

14. An apparatus as defined in claim 12 further comprising a temperature controller coupled to each of the lasers for tuning the lasers by temperature control to achieve to resolution less than 250 MHz.

15. A laser module comprising:
a first laser assembly including a first laser for generating a first laser beam;
a second laser assembly including a second laser for generating a second laser beam;
a first tone generator for applying a first low frequency tone to the first laser;
a second tone generator for applying a second low frequency tone, different from said first tone, to the second laser;
a first beam splitter for combining the output of said first and second lasers to generate first and second combined beams;
a beam splitter assembly comprising second and third beam splitters respectively disposed in the paths of said first and second combined beams for respectively splitting said first and second combined beams into third and fourth combined optical beams;
first and second photodiodes in the path of said third and fourth combined optical beams respectively, and each photodiode having a respective output; and a processor for comparing the respective outputs of said first and second photodiodes for computing the wavelength of said first and second lasers.

16. A method for determining the respective wavelengths of the frequency sources in a multi-frequency composite optical beam comprising:
applying a first low frequency tone to the first laser;
applying a second low frequency tone, different from said first tone, to the second laser;
combining the beams from said first and second lasers to generate first and second combined beams;
splitting said first combined beam into a third combined optical beam;
splitting said second combined beam into a fourth combined optical beam;
detecting the power of said third combined optical beam using a first photodiode having a first spectral response;
detecting the power of said fourth combined optical beam using a second photodiode having a second spectral response; and
comparing the respective outputs of said first and second photodiodes and computing the wavelengths of said first and second lasers.

17. A method as defined in claim 16, further comprising filtering at least one of said third and fourth combined optical beams with an optical filter with a predetermined spectral response.

* * * * *